United States Patent [19]

Durlach

[11] 4,355,043

[45] Oct. 19, 1982

[54] NOVEL DERIVATIVES OF 3-AMINOPROPANESULFONIC ACID HAVING A REINFORCED ACTIVITY ON MEMBRANE

[75] Inventor: Jean P. Durlach, Paris, France

[73] Assignee: Les Laboratoires Meram, France

[21] Appl. No.: 150,946

[22] Filed: May 19, 1980

[30] Foreign Application Priority Data

May 23, 1979 [FR] France ............................ 79 13207

[51] Int. Cl.³ ..................... A61K 31/315; C07F 3/06
[52] U.S. Cl. ............................ 424/289; 260/429.9; 260/513 N; 424/303
[58] Field of Search ..................... 260/513 N, 429.9

[56] References Cited

U.S. PATENT DOCUMENTS

| | | | |
|---|---|---|---|
| 3,039,916 | 6/1962 | Neracher et al. | 260/513 N |
| 3,544,597 | 12/1970 | Killam | 260/513 N X |
| 4,233,229 | 11/1980 | Chakrabarti | 260/513 N X |

FOREIGN PATENT DOCUMENTS 2321285 3/1977 France .
2384751 10/1978 France .

OTHER PUBLICATIONS

Chemical Abstracts 65 20373e (1966), 67 11213f (1967), 75 37386e (1971), 89 39924s (1978).

*Primary Examiner*—Helen M. S. Sneed
*Attorney, Agent, or Firm*—Bacon & Thomas

[57] ABSTRACT

The present invention relates to novel salts of sodium, potassium, lithium, calcium, magnesium, zinc of N-acetylhomotaurine having a reinforced activity on membrane, to the process for preparation thereof and to their application as neurotropic, vasculotropic and antiasthenic medicaments.

8 Claims, No Drawings

NOVEL DERIVATIVES OF 3-AMINOPROPANESULFONIC ACID HAVING A REINFORCED ACTIVITY ON MEMBRANE 3-aminopropanesulfonic acid (3-APS or homotaurine) possesses, like its lower homologue 2-aminoethanesulfonic acid (or taurine), biological, and particularly neuromuscular and vasculo-metabolic properties. These seem to depend on its properties of membrane stabilisation which have been demonstrated for the 3-APS, whilst their importance was already known for taurine.

This analogy between the two homologues (3-APS and taurine) cannot conceal the profound differences existing between these two molecules. Taurine is a physiological molecule present and active in the organism, whilst 3-APS does not exist therein spontaneously. Moreover, the biological properties of the two molecules are known to be qualitatively and quantitatively different.

If the polarity of the molecule of 3-APS is modified, by blocking the primary amine by acetylation, stable and well-defined salts may be obtained.

It has surprisingly been found that the novel salts of 3-acetylaminopropanesulfonic acid according to the invention present a reinforced stabilising activity on membrane.

The invention therefore relates to derivatives of 3-APS (or homotaurine) of formula:

[CH$_3$CONH—(CH$_2$)$_3$—SO$_3$]$_n$M    (I)

in which M represents an atom of alkali metal, i.e. sodium, potassium or lithium, and, in these cases, n is equal to 1, or an atom of magnesium, calcium or zinc, and, in these cases, n is equal to 2, and to the application thereof as medicaments.

The invention also relates to a process for preparing the derivatives of formula I, wherein the base M(OH)$_n$ and the 3-APS acid are dissolved in water, possibly in the presence of acetic acid; acetic anhydride is then introduced into the solution obtained, so as to maintain a temperature of 30° to 40° C. and the mixture is left to react at this temperature for about 1 hour. The solution obtained is concentrated to dryness, the residue is redissolved in distilled water and the solution concentrated to dryness again in order to obtain the product in the form of a crystalline powder.

The following examples are intended to illustrate the process for preparing the compounds according to the invention.

EXAMPLE I

Preparation of sodium N-acetylhomotaurinate (3-acetylaminopropanesulfonate of sodium)

CH$_3$CO—NH—CH$_2$—CH$_2$—CH$_2$—SO$_3$Na

In a 4 liter flask provided with stirring means, a bromine funnel and a thermometer, 1,216 g of 17.5% sodium hydroxide solution and 750 g of homotaurine are added.

After complete dissolution, at a temperature of between 25° and 40° C., 630 g of acetic anhydride are added so as not to exceed a temperature of between 30° and 40° C. The mixture is then maintained at this temperature by heating for at least 1 hour.

The solution is then concentrated in vacuo, the residue is redissolved in 2.5 l of distilled water and the mixture is concentrated again. The residue is then dissolved in 1.6 l of distilled water, filtered, then concentrated almost completely.

Drying is terminated in an oven in vacuo. A colourless crystalline powder is obtained.

Yield 92%, M.P. 140°–150° C.—Content of water 2.4%

| | Analysis % calculated | % found |
|---|---|---|
| Nitrogen | 6.89 | 6.80 |
| Sodium | 11.33 | 11.06 |

EXAMPLE 2

Preparation of potassium N-acetylhomotaurinate (3-acetylaminopropanesulfonate of potassium)

CH$_3$CO—NH—CH$_2$—CH$_2$—CH$_2$SO$_3$K

In the same apparatus as for the preceding salt, 1,700 g of 15.4% potassium hydroxide solution and 650 g of homotaurine are introduced.

After dissolution, 552 g of acetic anhydride are introduced, the temperature remaining between 30° and 40° C. This temperature is then maintained for 1 hour. The solution obtained is concentrated in vacuo, the residue is redissolved in 2.150 l of distilled water.

After a new concentration, the product is redissolved in 1.5 l of distilled water, filtered, then concentrated almost completely. Drying is terminated in an oven in vacuo. A colourless crystalline powder is obtained.

Yield: 96%, m.p. 205°–207° C.—Water content: 1.6%

| | Analysis % calculated | % found |
|---|---|---|
| Nitrogen | 6.38 | 6.27 |
| Potassium | 17.84 | 17.39 |

EXAMPLE 3

Preparation of lithium N-acetylhomotaurinate

CH$_3$CO—NH—CH$_2$—CH$_2$—CH$_2$—SO$_3$Li 1,242 g of 10.5% lithium hydroxide solution and 750 g of homotaurine are introduced into the same apparatus as before.

Under the same conditions as for the preceding salts, 630 g of acetic anhydride are added and the treatment is carried out according to the modus operandi indicated hereinabove. A colourless crystalline powder is obtained.

Yield: 95%, m.p. 294°–296° C.—Water content: 0.6%

| | Analysis % calculated | % found |
|---|---|---|
| Nitrogen | 7.48 | 7.39 |

| | Analysis | |
|---|---|---|
| | % calculated | % found |
| Lithium | 3.7 | 3.56 |

EXAMPLE 4

Preparation of calcium N-acetylhomotaurinate $(CH_3CO-NH-CH_2-CH_2-CH_2-SO_3)_2Ca$ 200 ml of distilled water, 19.7 g of calcium hydroxide, 32 g of acetic acid and 75 g of homotaurine are introduced into a 3-necked 1 liter flask.

Stirring is effected at a temperature of between 25° and 40° C. until dissolution, then 63 g of acetic anhydride are introduced, so as not to exceed a temperature of between 30° and 40° C. This temperature is then maintained for 1 hour. The solution obtained is treated as in the preceding preparations. A colourless crystalline powder is obtained.

Yield: 90%, m.p. about 270° C. (not clear)—Water content 3.6%

| | Analysis | |
|---|---|---|
| | % calculated | % found |
| Nitrogen | 7 | 6.8 |
| Calcium | 10 | 9.7 |

EXAMPLE 5

Preparation of magnesium N-acetylhomotaurinate $(CH_3CO-NH-CH_2-CH_2-CH_2-SO_3)\,Mg$ 45 ml of distilled water, 2.74 g of pure magnesium oxide, 8.2 g of acetic acid and 19 g of homotaurine are introduced into a three-necked 250 ml flask.

Stirring is effected at a temperature of between 25° and 40° C. until dissolution, then 15 g of acetic anhydride are introduced so as to obtain a temperature of between 30° and 40° C. This temperature is then maintained for one hour. The solution obtained is treated as in the preceding preparations.

At the end of concentration, a product of syrupy consistency is obtained. After drying in vacuo, the amorphous product is ground and dried again. A colourless powder is obtained.

Yield 90%

| | Analysis | |
|---|---|---|
| | % calculated | % found |
| Nitrogen | 7.28 | 7.06 |
| Magnesium | 6.32 | 6.16 |

EXAMPLE 6

Preparation of zinc N-acetylhomotaurinate $(CH_3CO-NH-CH_2-CH_2-CH_2-SO_3)_2Zn$

This salt is prepared in the same manner as the preceding ones; a product is obtained whose analysis is as follows:

| | Analysis | |
|---|---|---|
| | % calculated | % found |
| Nitrogen | 6.6 | 5.82 |
| Zinc | 15.3 | 14.48 |

Any other salt of metals or organic bases such as papaverines, ethanolamine, vincamine, etc., may also be prepared by the same process.

PHARMACOLOGICAL PROPERTIES

The toxicity of the derivatives according to the invention have been studied in the male mouse. Table I hereinbelow gives the $LD_{50}$ by intraperitoneal route expressed in g/kg of substance and in mg of ion/kg. The stabilising action of the compounds of the invention has been studied on the erythrocyte membrane in vitro by the conventional method of J. H. Brown et coll., Proc.-Soc.Exp.Biol.Med. (1967)125, 837 to 842; and W. Mikikits et coll. Nature (1970) 225, Mar. 21, 1150–1151. This method makes it possible to demonstrate a stabilising effect on the red cell membrane of the rabbit, by studying the rate of haemolysis, during incubation in hypotonic medium (10 mM phosphate buffer—pH 7.4—NaCl 5.5 g/l) and with heat (53° C.). The products to be studied are added to the incubation medium at different concentrations. The rate of haemolysis is compared with that of a control. The $ED_{50}$ is thus determined and the values obtained are given in Table II hereinbelow in mM/l. This Table shows that the novel derivatives according to the invention present a stabilisation activity on the membrane greater than that of 3-APS (homotaurine). Whilst the $ED_{50}$ of homotaurine is 15 mM/l, that of the compounds according to the invention varies from 1 to 10; it is therefore always less than that of homotaurine and up to 15 times less. It is obvious that this pharmacological property of all the derivatives according to the invention is translated by properties common thereto; however, according to the nature of the cation, the compounds present singularities which enable certain salts to be used in certain applications rather than others.

Thus, in the rat, whilst homotaurine by the intraperitoneal route does not modify the rectal temperature, the derivatives according to the invention all cause a hypothermia. However, the salts of bivalent cations are more active than those of monovalent cations and that of calcium more active than that of magnesium. This same ranking is found in the antagonism exerted by the compounds according to the invention on the motive excitation obtained in the mouse by ethanol.

The anatagonism of the acetylhomotaurinates according to the invention vis-à-vis the hypermotility caused by ethanol has been studied by the test of Cott-Carlsson Engel Lindqvist, Naunyn-Schmiedeberg's Archives of Pharmacology 295, 203–209 (1976); Female mice, distributed in batches of 9, receive the products to be tested per os one hour before the intraperitoneal injection of a solution of ethanol. The motility of the mice placed in the actimeter is recorded immediately after this injection, every 5 minutes, for 60 minutes. The percentage of variation of the motility of the mice treated with ethanol with respect to the controls receiving water is determined, and of mice treated with the product to be tested and with ethanol with respect to mice receiving only ethanol.

The products according to the invention have been studied, in this test, at the following doses: 80,100,200, 400 and 800 mg/kg per os. The results are as follows: The sodium acetylhomotaurinate proves to be the least active (at a dose of 400 mg/kg: slight antagonism which appears at the 50th minute of observation). The calcium acetylhomotaurinate manifests, at a dose of 200 and 400 mg/kg, a significant antagonism on the hypermotility by ethanol; this effect is confirmed at the dose of 800 mg/kg but does not appear to be superior to that recorded at 400 mg. At the doses of 200 and 400 mg/kg, the antagonistic effect of magnesium acetylhomotaurinate is slightly less than that of the calcium salt.

It should be noted that, at the same doses, the corresponding salts of the acetyltaurine present only little or no antagonistic effect in this test of hypermotility by ethanol.

The results are summarized in Table III hereinbelow.

The compounds according to the invention also present an anti-convulsivant action on the convulsions caused in the mouse by pentetrazol: After administration of pentetrazol, the time of appearance of the convulsions and the time of appearance of death is measured, in the animals which previously received, by the intraperitoneal route, the product to be tested, comparatively to controls receiving only pentetrazol.

The results are as follows. At the respective doses of 292 mg and 315 mg/kg (i.p.), the sodium and potassium acetylhomotaurinates increase, without reaching the level of significance, the time of appearance of the convulsions and that of death. However, magnesium acetylhomotaurinate is active at 400 mg/kg (i.p.) (significant on the time of appearance of death) and at 800 mg/kg (i.p.) (significant on the time of appearance of convulsions). The calcium acetylhomotaurinate manifests, at 400 and 800 mg/kg (i.p.) a significant antagonism (xx) on the time of appearance of death; the effect on the time of appearance of the convulsions is significant only at the dose of 800 mg/kg; it is very significant (xxx) at the dose of 1000 mg/kg.

In summary, the anti-convulsivant activity of Ca acetylhomotaurinate is, like the sedative activity, greater than that of Mg acetylhomotaurinate.

It should be noted that, measured by the same test, the corresponding activity of the salts of acetyltaurine is very clearly less, at the same doses, than that of the corresponding acetylhomotaurinates; Ca acetyltaurinate acting significantly (x) on the time of appearance of death only at the dose of 1000 mg mg/kg (i.p.) and Mg acetyltaurinate acting significantly (xx) on the times of appearance of the convulsions and of death only at the dose of 1000 mg/kg likewise.

The magnesium and lithium salts are distinguished in that they significantly reduce the toxicity of their cation. The $LD_{50}$ by the intraperitoneal route in the mouse is, expressed in $Mg^{++}$, 94 mg for the magnesium chloride and, expressed in $Li^{+}$, 88 mg for the lithium carbonate (reference salts). This $LD_{50}$ is significantly increased for the compounds according to the invention: magnesium acetylhomotaurinate: 161 mg and lithium acetylhomotaurinate: 157 mg.

On the other hand, the potassium salt proves in the rate to be the most active in the test of the muscle fatigued by application of lactic acid. The sodium salt by the oral route comes at the top of the series for the potentialization in the mouse of narcosis by ethanol. It is furthermore suitable for the manufacture of aqueous solutions.

THERAPEUTIC APPLICATION

The various compounds according to the invention may be administered by the general and local routes and in all forms: tablets, cachets, capsules, suspensions, solutions, syrups. For the local route, particular emphasis should be given to eye washes in aqueous solution, nose drops, ointments and aerosols.

The therapeutic indications may be slightly different according to the properties of the cation.

The calcium salt may be used as neurotropic agent; the magnesium salt as vasculotropic agent; the potassium salt as antiasthenic agent; the lithium salt may be used in for bipolar patients and the sodium salt in local treatments; the zinc salt may be used in dermatology.

By way of example, posology is at the usual doses of 1 g/day per os or by the parenteral route.

For example, the magnesium acetylhomotaurinate has been used in the form of sectile cachets of 0.50 g at the average usual dose of 1 g per 24 hours, which may be reduced by half or, on the contrary, widely exceeded up to 5 g/day. For parenteral route, ampoules of aqueous solution of acetylhomotaurinate may be used, for example of magnesium at 1 g per 10 ml, in slow intravenous route, due to the impression of heat that they give, or, better, in perfusions, intramuscular or sub-cutaneous. The doses vary from one intramuscular ampoule per day to a maximum of ten ampoules in slow perfusion under hospital conditions.

TABLE I

| Toxicity | | |
|---|---|---|
| $LD_{50}$ (male mouse, i.p.) | g/kg | mg cation/kg |
| Sodium acetylhomotaurinate | greater than 5 g | |
| Potassium acetylhomotaurinate | 4.12 g | 733 mg |
| Lithium acetylhomotaurinate | 4.26 g | 157 mg |
| Calcium acetylhomotaurinate | 1.87 g | 186 mg |
| Magnesium acetylhomotaurinate | 2.57 g | 161 mg |

(Calcium acetyltaurinate: $LD_{50}$ by oral route = 13.09 g/kg)

TABLE II

| Stabilising effect on the erythrocyte membrane of the rabbit | |
|---|---|
| | $ED_{50}$, expressed in mM/l |
| Homotaurine | 15 |
| Sodium acetylhomotaurinate | 5 |
| Potassium acetylhomotaurinate | 5 |
| Lithium acetylhomotaurinate | 10 |
| Magnesium acetylhomotaurinate | 10 |
| Calcium acetylhomotaurinate | 1 |

TABLE III

| Antagonism of the hyper motility by ethanol | | | |
|---|---|---|---|
| Products | Doses (per os) | Results | Significance |
| Calcium acetyl-homotaurinate | 80 mg | 0 | |
| | 100 mg | antagonism | xxx |
| | 200 mg | antagonism | xx |
| | 400 mg | antagonism | x |
| | 800 mg | antagonism | xx (shorter) |
| Magnesium acetyl-homotaurinate | 80 mg | antagonism | x |
| | 100 mg | antagonism | not significant |
| | 200 mg | antagonism | x |
| | 400 mg | antagonism | x |
| Sodium acety-homotaurinate | 400 mg | slight antagonism | not significant |
| Magnesium acetyl-taurinate | 100 mg | antagonism | not significant |
| | 200 mg | antagonism | not significant |
| | 400 mg | 0 | |
| Calcium acetyl-taurinate | 80 mg | 0 | |
| | 400 mg | 0 | |
| | 800 mg | antagonism | x to xx according |

TABLE III-continued

| Antagonism of the hyper motility by ethanol | | | |
|---|---|---|---|
| Products | Doses (per os) | Results | Significance |
| Sodium acetyl-taurinate | 400 mg | 0 | to the time |

What is claimed is:

1. Derivatives of 3-aminopropanesulfonic acid, represented by the formula

[CH$_3$CONH—(CH$_2$)$_3$SO$_3$]$_n$M in which M represents a member selected from the group consisting of sodium, potassium, lithium, calcium, magnesium and zinc, n being equal to 1 or 2.

2. The derivative of claim 1, which is sodium N-acetylhomotaurinate.

3. The derivative of claim 1, which is potassium N-acetylhomotaurinate.

4. The derivative of claim 1, which is lithium N-acetylhomotaurinate.

5. The derivative of claim 1, which is magnesium N-acetylhomotaurinate.

6. The derivative of claim 1, which is calcium N-acetylhomotaurinate.

7. A pharmaceutical composition, for use as a neurotropic, vasculotropic or antiasthenic medicament, comprising an effective amount of the derivative of claim 1, and a pharmaceutically acceptable excipient, for administration by the oral, parenteral or local route.

8. Process for preparing the derivatives of claim 1, comprising the steps of dissolving 3-aminopropanesulfonic acid in a solution of the base M(OH)$_n$, possibly with the addition of acetic acid, introducing acetic anhydride in the solution so as to maintain the temperature between 30° and 40° C., maintaining this temperature for about one hour, concentrating the solution obtained to dryness to obtain the product which is purified by dissolution in water, and further concentrating the solution to dryness.

* * * * *